United States Patent [19]

Danree et al.

[11] Patent Number: 4,960,900

[45] Date of Patent: Oct. 2, 1990

[54] OXYIMINO DERIVATIVES OF THIAZOLE, METHOD OF PREPARATION AND USE IN THERAPY

[75] Inventors: Bernard Danree, Poissy; Patrick Houziaux, Bazemont; Jean-Yves Lacolle, La Celle Saint Cloud; Jean-Pierre Riffaud, Versailles, all of France

[73] Assignee: Institut de Ercherches Chimiques et Biologiques Appliquees (I.R.C.E.B.A.), Vicq, France

[21] Appl. No.: 290,248

[22] Filed: Dec. 23, 1988

[30] Foreign Application Priority Data

Dec. 23, 1987 [FR] France .................. 87 18056

[51] Int. Cl.$^5$ .................. C07D 277/28; C07D 417/12
[52] U.S. Cl. .................. 548/203; 540/603; 544/60; 544/133; 544/367; 546/209; 548/204
[58] Field of Search .......... 548/203, 204; 546/209; 544/60, 133, 367; 540/603

[56] References Cited

U.S. PATENT DOCUMENTS 4,363,813 12/1982 Kagaki .................. 548/203

FOREIGN PATENT DOCUMENTS 2056440 3/1981 United Kingdom .

OTHER PUBLICATIONS

Chemical Abstracts, vol. 48, No. 6, 25/03/54, Col. 3294-95.
Suzuki, J. Pharm. Soc. Japan 73 394 (1953).

*Primary Examiner*—Robert Gerstl
*Attorney, Agent, or Firm*—Burgess,-Ryan & Wayne

[57] ABSTRACT

The present invention relates, by way of novel industrial products, to the following oxyimino derivatives of thiazole: (a) the E and Z diastereoisomers of the formula

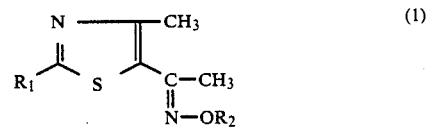

in which $R_1$ represents H, F, Cl, Br, $CF_3$ or $CH_3$ and $R_2$ represents a $C_1$-$C_{10}$-alkyl group, a benzyl group of the formula $CH_2C_6H_2(R_3)_3$, in which each $R_3$ identical or different represents H, F,Cl,Br, $CF_3$, a $C_1$-$C_4$-alkyl group or a $C_1$-$C_4$-alkoxy group, a group $CH_2COOR_4$, in which $R_4$ represents H, a $C_1$-$C_4$-alkyl group or the ammonium group, $NH_4^+$, a group $CH_2COOM_m$, in which M is an alkali metal or alkaline earth metal and m is its valency, or a 2-aminoethyl group of the formula $CH_2CH_2NR_5R_6$, in which $R_5$ and $R_6$, which can be identical or different each represent H or a $C_1$-$C_4$-alkyl group, it being possible for $R_5$ and $R_6$, taken together with the nitrogen atom to which they are bonded, to form a 5-to 7-membered N-heterocyclic group which may contain a second heteroatom selected from N, O and S and may be substituted, it also being possible for $R_2$ to represent the hydrogen atom when $R_1$ is other than H, and mixtures of the said E and Z isomers; and (b) the addition salts of the said E and Z isomers and of mixtures thereof.

These novel derivatives, as well as the compound of formula I in which $R_1 = R_2 = H$, are useful in therapy as anticonvulsants.

8 Claims, No Drawings

OXYIMINO DERIVATIVES OF THIAZOLE, METHOD OF PREPARATION AND USE IN THERAPY

FIELD OF THE INVENTION

The present invention relates, by way of novel industrial products, to oxyimino derivatives of thiazole which are the 5-(1-alkoxyimino- and 1-hydroxyimino-ethyl)-4-methylthiazoles of formula I below and addition salts thereof. It further relates to the method for the preparation of these products and to their use in therapy, especially as anticonvulsants.

PRIOR ART

It is known that numerous thiazole derivatives have been described in the past and that a restricted number of these derivatives have anticonvulsant properties.

It is known, in particular from French patent document A-945 198, British patent document A-641 426 and U.S. patent document A-2,654,760, that 5-(2-hydroxyethyl)-4-methylthiazole is a useful synthesis intermediate in the preparation of vitamin B1; it is further known, especially from the summary in Chemical Abstracts 74, 141 617 w, that its isomer 1-(4-methylthiazol-5-yl)ethanol possesses anticonvulsant properties.

It is known, especially from French patent document A-2 555 583, that 2-(4-methylthiazol-5-yl)propan-2-ol has anticonvulsant and antihypoxic properties while one of its lower homologs, namely 5-hydroxymethyl-4-methylthiazole, is devoid of anticonvulsant effects and its other lower homolog, namely 1-(4-methylthiazol-5-yl)ethanol mentioned above, which is an anticonvulsant, is devoid of beneficial antihypoxic effects.

Also, 5-(1-hydroxyiminoethyl)-4-methylthiazole is known from the article by M. SUZUKI et al., J. Pharm. Soc. Japan 73, 394–396 (1953). However, the said article neither describes nor suggests the possible pharmacological properties of this product and consequently does not consider its use in therapy as an anticonvulsant.

Furthermore, 2-piperazinoacetamido-4-methylthiazole derivatives useful as anticonvulsants are known from the French patent application filed in the name of the Applicant Company on 29 Jul. 1987 under no. 87 10 738.

SUMMARY OF THE INVENTION

The principal aim of the invention is to provide novel thiazole derivatives which are (i) structurally different from the compounds of the above-mentioned prior art, and (ii) useful in therapy with regard to their anticonvulsant properties.

According to the invention, a method for the preparation of these novel derivatives is also proposed, together with their use in therapy in the treatment of convulsions, especially convulsions of epileptic origin.

The novel oxyimino derviatives of thiazole according to the invention are selected from the group consisting of:

(i) the 5-(1-alkoxyimino- and 1-hydroxyimino-ethyl)-4-methylthiazoles of the formula

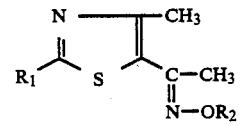

in which $R_1$ represents H, F, Cl, Br or $CH_3$ and $R_2$ represents a $C_1$–$C_{10}$-alkyl group, a benzyl group of the formula $CH_2C_6H_2(R_3)_3$, in which each $R_3$, identical or different represents H, F, Cl, Br, $CF_3$, a $C_1$–$C_4$-alkyl group or a $C_1$–$C_4$-alkoxy group, a group $CH_2COOR_4$, in which $R_4$ represents H, a $C_1$–$C_4$-alkyl group or the ammonium group, $NH_4^+$, a group $CH_2COOM_{m\rightarrow}$, in which M is an alkali metal or alkaline earth metal and m is its valency, or a 2-aminoethyl group of the formula $CH_2CH_2NR_5R_6$, in which $R_5$ and $R_6$, which can be identical or different, each represent H or a $C_1$–$C_4$-alkyl group, it being possible for $R_5$ and $R_6$, taken together with the nitrogen atom to which they are bonded, to form a 5- to 7-membered N-heterocyclic group which may contain a second heteroatom selected from N, O and S and may be substituted, it also being possible for $R_2$ to represent the hydrogen atom when $R_1$ is other than H;

(ii) the geometrical configurational isomers thereof; and (iii) the corresponding addition salts.

In its broadest aspect, the invention relates to the use as anticonvulsant drugs of, on the one hand, the products mentioned above and, on the other hand, 5-(1-hydroxyiminoethyl)-4-methylthiazole—the compound of formula I in which $R_1=R_2=H$—which has been described as a laboratory curiosity with no mention of its possible pharmaceutical properties in the article by M. SUZUKI cited above, and the E and Z isomers thereof and the corresponding addition salts.

DETAILED DESCRIPTION OF THE INVENTION

The invention therefore relates on the one hand to the E and Z geometrical isomers of formula I and mixtures thereof, and on the other hand to the addition salts of the said geometrical isomers and of mixtures thereof.

The existence of E and/or Z diastereoisomers is a result of the steric relationships at the non-cyclic C=N bond; for the E configuration (from the German "entgegen", i.e. "opposite") and Z configuration (from the German "zusammen", i.e. "together"), the priority group bonded to one of the atoms of the double bond is compared with the priority group bonded to the other atom of the said double bond, the two groups in the present case being the thiazol-5-yl group on the carbon atom and the group $OR_2$ on the nitrogen atom.

Addition salts are understood here to mean the acid addition salts obtained by reacting a free base of formula I with a mineral or organic acid. The following may be mentioned in particular among the acids which can be used to salify the free bases of formula I: hydrochloric, hydrobromic, acetic, formic, propionic, succinic, cinnamic, citric, methanesulfonic and p-toluenesulfonic acids. In general, the hydrochlorides are the preferred addition salts here for use in therapy as anticonvulsants.

The alkyl groups covered by the definition of $R_2$ are $C_1$–$C_{10}$ hydrocarbon radicals, preferably a $C_1$–$C_4$ lower alkyl group, with a linear or branched chain. By way of example, if $R_2$ represents an alkyl group, it can be especially a methyl, ethyl, n-propyl, i-propyl, n-butyl, s-butyl, t-butyl or 2-propylpentyl group. The preferred alkyl groups $R_2$ are $CH_3$, $C_2H_5$, i—$C_3H_7$ and n—$C_4H_9$.

Likewise, the alkyl groups covered by the definitions of $R_3$, $R_4$, $R_5$ and $R_6$ are $C_1$-$C_4$ hydrocarbon radicals with a linear or branched chain. The preferred alkyl groups $R_3$ and $R_4$ are the ethyl group and in particular the methyl group, and the preferred alkyl groups for $R_5$ and $R_6$ are the t-butyl, i-propyl and ethyl groups and in particular the methyl group.

The alkoxy groups covered by the definition of $R_3$ contain $C_1$-$C_4$ hydrocarbon radicals with a linear or branched chain which are monovalent and bonded to an oxygen atom. The methoxy, ethoxy, n-propoxy, i-propoxy, s-butoxy, i-butoxy, t-butoxy and n-butoxy groups are particularly suitable. The preferred alkoxy groups $R_3$ are the methoxy group and in particular the ethoxy group.

The N-heterocyclic groups covered by the definition of $NR_5R_6$ are preferably selected from the group consisting of the pyrrolidino, piperidino, morpholino, thiomorpholino, 4-methylpiperazino, 4-phenylpiperazino, 4-(4-chlorophenyl)piperazino, 4-(2-hydroxyethyl)-piperazino and hexamethyleneimino groups. These N-heterocyclic groups are saturated, i.e. they have no C=C or C=N double bonds, and contain from 5 to 7 ring members. The most advantageous N-heterocyclic groups from the pharmacological point of view are the piperidino, morpholino and, preferably, pyrrolidino groups.

Na, K and Ca may be mentioned in particular among the metals M which are suitable, sodium being the preferred metal here.

With regard to what has been stated above, the novel compounds which are preferred according to the invention are the compounds of formula I in which $R_1$ is H, Cl, Br or $CH_3$ and $R_2$ is $CH_3$, $C_2H_5$, i—$C_3H_7$, n—$C_4H_9$, $CH_2C_6H_2(R_3)_3$ (in which each $R_3$ identical or different, is H, F, Cl, Br, $CF_3$, $CH_3$, $CH_3O$ or $C_2H_5O$), $CH_2COONa$, $CH_2COOK$, $CH_2COOCH_3$, $CH_2COOC_2H_5$ $CH_2CH_2N(CH_3)_2$, $CH_2CH_2N(C_2H_5)_2$, 2-pyrrolidinoethyl, 2-morpholinoethyl or 2-piperidinoethyl, it being possible for $R_2$ to represent H if $R_1$ is other than H.

Among these compounds, the most advantageous from the pharmacological point of view are (i) the compounds of formula I in which $R_1$ is H and $R_2$ is $CH_3$, $C_2H_5$, i—$C_3H_7$, n—$C_4H_9$, $CH_2C_6H_4R_3$ (in which $R_3$ is H, F, Cl, Br, $CF_3$, $CH_3$, $CH_3O$ or $C_2H_5O$), $CH_2COONa$, $CH_2COOCH_3$, $CH_2COOC_2H_5$, $CH_2CH_2N(CH_3)_2$, $CH_2CH_2N(C_2H_5)_2$ or 2-pyrrolidinoethyl, and (ii) the compounds of formula I in which $R_1$ is Cl, Br or $CH_3$ and $R_2$ is H or $CH_3$.

Also advantageous from the pharmacological point of view is (iii) the compound of formula I in which $R_1=R_2=H$, which is described as a laboratory curiosity by M. SUZUKI et al. in the article cited above.

The compounds of formula I can be prepared according to a method known per se by the application of classical reaction mechanisms. The method which is recommended according to the invention consists in reacting a 5-acetyl-4-methylthiazole compound of the formula

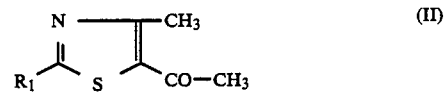

with a hydroxylamine derivative of the formula $H_2NOR_2$  (III)

in which $R_1$ and $R_2$ are defined as indicated above.

This reaction is advantageously carried out with an excess of III relative to the stoichiometric conditions. 1.2 to 1.8 mol (preferably 1.5 mol) of III will advantageously be used per mol of II, in the presence of sodium acetate, at a temperature of the order of 10° to 25° C. [especially at room temperature (15°–20° C.)], for at least 3 h, in order to perform the reaction II+III.

The sodium acetate participating in this reaction will advantageously be used in excess relative to the compound II. In practice, 1.2 to 1.8 mol and preferably 1.5 mol of anhydrous $CH_3CO_2Na$ will be used per mol of II. In other words, the reaction will be carried out using a molar amount of $CH_3CO_2Na$ which is substantially identical to that of the hydroxylamine derivative of formula III.

If necessary, the product of formula I in which $R_2=H$, obtained according to the said reaction II+III if the compound III is hydroxylamine, can be subjected to an O-alkylation reaction with a $C_1$-$C_4$ alcohol [so-called MITSUNOBU reaction described by S. BITTNER et al. in J. Chem. Soc. Perkin I, 1708 (1976)] in order to give a compound of formula I in which $R_2$ is other than the hydrogen atom.

The reaction mechanism is then as follows:

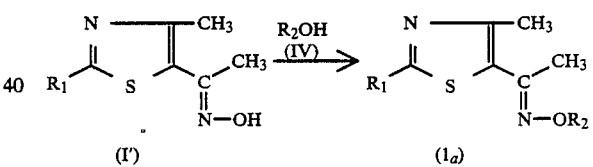

in which $R_1$ and $R_2$ are defined as indicated above, except that $R_2$ is other than H.

The reaction I'+IV is advantageously carried out using an excess amount of alcohol IV relative to the stoichiometric conditions, the alcohol $R_2OH$ acting both as reagent and as solvent or co-solvent.

In practice, this reaction is carried out in the presence of a phosphine (especially triphenylphosphine) and an azodicarboxylate (especially diethyl azodicarboxylate), at a temperature of between 10° and 25° C. [especially at room temperature (15°–20° C.)], for at least 5 h.

It will be even more advantageous to use about 1.5 mol of triphenylphosphine and about 2 mol of diethyl azodicarboxylate per mol of hydroxyimino compound I', and the alcohol $R_2OH$ will be a primary or secondary alcohol.

To summarize, the reaction II+III=I is the one which is recommended according to the invention in the sense that it applies to the synthesis of all the compounds of formula I. The alkoxyimino compounds of formula I (in which $R_2$ is other than H) can be prepared either according to the general reaction II+III=I mentioned above or according to the particular reaction I'+IV=$I_a$.

In view of the method of synthesis used, the compound of formula I according to the invention is generally a mixture of the E and Z diastereoisomers. The E and Z diastereoisomers can be isolated from the said mixture by a method known per se, especially by fractional distillation or fractional crystallization or, more advantageously, by column chromatography.

A number of typical compounds according to the invention have been collated in Table I below, without implying a limitation. The melting points which have been mentioned in this Table are instantaneous melting points determined on a Kofler bench.

The configuration of the products of Examples 1–9, and 11–29 was determined [cf. the weight ratio (and molar ratio) of the E/Z mixture in the said Table I]. As the configuration of the products of Example 10 was not studied, it is assumed that they are mixtures of E and Z isomers rather than the said E or Z isomers in the pure state; for the said products of Example 10, it is assumed that the Analysis of the product of Example 2 shows that it is an E/Z mixture in a weight ratio (and molar ratio) of 90/10. The product of Example 3 is the pure E isomer which was obtained from the product of Example 2 by column chromatography.

TABLE I $$\underset{R_1}{\overset{N}{\diagup}}\overset{}{\underset{S}{\diagdown}}\overset{CH_3}{\underset{\overset{\|}{C-CH_3}}{C=}}\overset{}{\underset{N-OR_2}{}}$$

| Product | Code no. | $R_1$ | $R_2$ | E/Z (%) | M.p. (°C.) or $n_D$ |
|---|---|---|---|---|---|
| Ex. 1 (a) | B-1 222 | H | $CH_3$ | 91/9 | $n_D^{25°C.}$ = 1.5528 (e) |
| Ex. 2 (b) | B-1 044 | H | $CH_3$ | 90/10 | M.p. = 100–105 (f) |
| Ex. 3 (a, d) | B-1 234 | H | $CH_3$ | 100/0 | M.p. = 90–95 (f) |
| Ex. 4 (a) | B-1 229 | H | $CH_2CH_3$ | 81/19 | $n_D^{21°C.}$ = 1.5395 (g) |
| Ex. 5 (b) | B-1 235 | H | $CH_2CH_3$ | 85/15 | M.p. = 95–100 (f) |
| Ex. 6 (a) | B-1 264 | H | $CH(CH_3)_2$ | 86/14 | $n_D^{21°C.}$ = 1.5285 |
| Ex. 7 (b) | B-1 265 | H | $CH(CH_3)_2$ | 86/14 | M.p. = 100–103 (f) |
| Ex. 8 (a) | B-1 266 | H | $(CH_2)_3CH_3$ | 89/11 | $n_D^{21°C.}$ = 1.5275 |
| Ex. 9 (b) | B-1 233 | H | $(CH_2)_3CH_3$ | 98/2 | M.p. = 68–73 (h) |
| Ex. 10 (a) | B-1 384 | H | $CH_2CH(C_3H_7)_2$ | — | — |
| Ex. 11 (a) | B-1 255 | H | $CH_2$–C$_6$H$_5$ | 89/11 | $n_D^{21°C.}$ = 1.5919 (i) |
| Ex. 12 (b) | B-1 262 | H | $CH_2$–C$_6$H$_5$ | 98/2 | M.p. = 103–104 (j) |
| Ex. 13 (a) | B-1 375 | H | $CH_2$–C$_6$H$_4$–F | 85/15 | $n_D^{20°C.}$ = 1.5772 (k) |
| Ex. 14 (a) | B-1 376 | H | $CH_2$–C$_6$H$_4$–Cl | 82/18 | $n_D^{21°C.}$ = 1.5960 (l) |
| Ex. 15 (a) | B-1 379 | H | $CH_2$–C$_6$H$_4$–CH$_3$ | 87/13 | $n_D^{21°C.}$ 1.5909 (g) |
| Ex. 16 (a) | B-1 377 | H | $CH_2$–C$_6$H$_4$–CF$_3$ | 85/15 | $n_D^{21.5°C.}$ = 1.5370 (z) |

TABLE I-continued $$R_1 - C(=N) - S - C(CH_3) = C(CH_3) - C(=N-OR_2) - CH_3$$

| Product | Code no. | R₁ | R₂ | E/Z (%) | M.p. (°C.) or $n_D$ |
|---|---|---|---|---|---|
| Ex. 17 (a) | B-1 378 | H | CH₂-C₆H₄-OEt | 85/15 | $n_D^{20°C.} = 1.5809$ (aa) |
| Ex. 18 (a) | B-1 290 | H | CH₂COOCH₃ | 91/9 | $n_D^{21°C.} = 1.5385$ (m) |
| Ex. 19 (a, n) | B-1 329 | H | CH₂COONa | 99.5/0.5 | M.p. = 205–207 (o) |
| Ex. 20 (c, n) | B-1 296 | H | CH₂CH₂N(CH₃)₂ | 98/2 | M.p. = 160–165 (p) |
| Ex. 21 (a) | B-1 304 | H | CH₂CH₂–N(pyrrolidinyl) | 98/2 | $n_D^{22°C.} = 1.5502$ (q) |
| Ex. 22 (a) | B-1 097 | Cl | H | 97/3 | M.p. = 141–142 (r) |
| Ex. 23 (a) | B-1 077 | Br | H | 85/15 | M.p. = 149–150 (s) |
| Ex. 24 (a) | B-1 193 | Cl | CH₃ | 90/10 | $n_D^{21°C.} = 1.5617$ (t) |
| Ex. 25 (a) | B-1 267 | Br | CH₃ | 80/20 | (u) |
| Ex. 26 (a) | B-1 061 | CH₃ | CH₃ | 98/2 | $n_D^{25.6°C.} = 1.5408$ |
| Ex. 27 (b) | B-1 042 | CH₃ | CH₃ | 98/2 | M.p. = 130–135 (o) |
| Ex. 28 (a, v) | B-1 876 | H | H | 99/1 | M.p. = 142–143 (w) |
| Ex. 29 (b) | B-1 026 | H | H | 99/1 | M.p. = 185–188 (x) |

Notes
(a): free base
(b): monohydrochloride
(c): dihydrochloride
(d): pure E isomer
(e): B.p.$_{0.22\ mm\ Hg}$ = 72–74° C.
(f): solvent of recrystallization: AcOEt
(g): B.p.$_{0.20\ mm\ Hg}$ = 58–62° C.
(h): solvent of recrystallization: hexane/AcOEt mixture (1/1 v/v)
(i): B.p.$_{0.10\ mm\ Hg}$ = 130–132° C.
(j): solvent of recrystallization: AcOEt
(k): B.p.$_{0.15\ mm\ Hg}$ = 110–115° C.
(l): B.p.$_{0.10\ mm\ Hg}$ = 125–130° C.
(m): B.p.$_{0.15\ mm\ Hg}$ = about 98° C.
(n): monohydrate
(o): solvent of recrystallization: AcOEt/isopropanol (1/1 v/v)
(p): solvent of recrystallization: AcOEt/EtOH (1/1 v/v)
(q): B.p.$_{0.20\ mm\ Hg}$ = 108–110° C.
(r): solvent of recrystallization: n-butanol
(s): solvent of recrystallization: toluene
(t): B.p.$_{0.15\ mm\ Hg}$ = 70–72° C.
(u): B.p.$_{0.12\ mm\ Hg}$ = 82–83° C.
(v): described as a product by M. SUZUKI et al.
(w): solvent of recrystallization: MeOH
(x): solvent of recrystallization: isopropanol
(y): B.p.$_{C.1\ mm\ Hg}$ = 128–134° C.
(z): B.p.$_{C.15\ mm\ Hg}$ = 110–115° C.
(aa): B.p.$_{0.1\ mm\ Hg}$ = 134–138° C.
Comments:
The pressure values 0.10 mm Hg, 0.12 mm Hg, 0.15 mm Hg, 0.20 mm Hg and 0.22 mm Hg correspond to about 13.3 Pa, 15.9 Pa, 19.9 Pa, 26.6 Pa and 29.3 Pa respectively.

The best way of carrying out the invention consists in using 5-(1-methoxyiminoethyl)-4-methylthiazole, 5-(1-benzyloxyiminoethyl)-4-methylthiazole and the non-toxic addition salts thereof as novel industrial products useful in therapy, the most advantageous products being a) the mixture E/Z=91/9 of the above-mentioned methoxyimino derivative (free base of Example 1; code no.: B-1 222), b) the mixture E/Z=90/10 of the corresponding hydrochloride (monohydrochloride of Example 2; code no.: B-1 044), c) the mixture E/Z=89/11 of the above-mentioned benzyloxyimino derivative (free base of Example 11; code no.: B-1 255) and d) the mixture E/Z=98/2 of the corresponding hydrochloride (monohydrochloride of Example 12; code no.: B-1 262). The pure E isomer (ratio E/Z=100/0) of the said methoxyimino derivative (free base of Example 3; code no.: B-1 234) is also advantageous but is less active than the corresponding mixture E/Z=91/9 as an anticonvulsant.

The compounds according to the invention, namely on the one hand the E and Z isomers and mixtures thereof of formula I bis below, and on the other hand the addition salts thereof, are useful in therapy. They act as anticonvulsant active ingredients and are therefore recommended in the treatment of convulsions, and especially convulsions of epileptic origin, in man.

According to the invention, a therapeutic composition is therefore recommended which contains, in association with a physiologically acceptable excipient, at least one compound selected from (a) the E and Z diastereoisomers and mixtures thereof of the formula

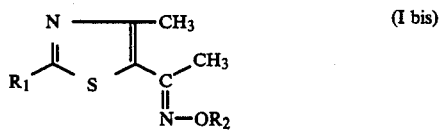 (I bis)

in which $R_1$ represents H, F, Cl, Br or $CH_3$ and $R_2$ represents H, a $C_1$–$C_{10}$-alkyl group, especially a $C_1$–$C_4$ lower alkyl group, a benzyl group of the formula $CH_2C_6H_2(R_3)_3$ in which each $R_3$, identical or different, represents H, F, Cl, Br, $CF_3$, a $C_1$–$C_4$ alkyl group or a $C_1$–$C_4$ alkoxy group, a group $CH_2COOR_4$, in which $R_4$ represents H, a $C_1$–$C_4$-alkyl group or the ammonium group, $NH_4^+$, a group $CH_2COOM_{m\rightarrow}$, in which M is an alkali metal or alkaline earth metal and m is its valency, or a 2-aminoethyl group of the formula $CH_2CH_2NR_5R_6$, in which $R_5$ and $R_6$, which can be identical or different, each represent H or a $C_1$–$C_4$-alkyl group, it being possible for $R_5$ and $R_6$, taken together with the nitrogen atom to which they are bonded, to form a 5- to 7-membered N-heterocyclic group which may contain a second heteroatom selected from N, O and S and may be substituted; and (b) the non-toxic addition salts thereof.

Of course, in a composition of this type, the active principle is present in a therapeutically effective amount.

According to the invention, a therapeutic use is also recommended in which an anticonvulsant drug for use in therapy in the treatment of convulsions, especially convulsions of epileptic origin, is prepared from a substance selected on the one hand from the E and Z isomers of the 5-(1-alkoxyimino- and 1-hydroxyiminoethyl)-4-methylthiazoles of formula I bis and mixtures thereof, and on the other hand from the non-toxic addition salts thereof.

Further advantages and characteristics of the invention will be understood more clearly from the following description of Preparative Examples and results of toxicological and pharmacological tests. These data as a whole are given by way of illustration and do not imply a limitation.

PREPARATION I

Preparation of
5-(1-methoxyiminoethyl)-4-methylthiazole (Example 1; code no.: B-1 222)

141.18 g (1 mol) of 5-acetyl-4-methylthiazole and 1410 ml of methanol are introduced into a four-liter three-necked flask provided with a condenser, a thermometer, a dropping funnel and a pneumatic stirrer. 125.28 g (1.5 mol) of methoxylamine hydrochloride dissolved in 250 ml of water are added dropwise to the resulting solution. The medium is stirred for 0.5 h and 123.06 g (1.5 mol) of anhydrous sodium acetate are then added in portions to the resulting mixture.

The reaction medium obtained is stirred at room temperature (15°–20° C.) for 12 h and then filtered on a glass frit to remove the sodium chloride formed. The filtrate collected is concentrated to dryness under vacuum and the resulting residue is taken up with methylene chloride. The insoluble material is separated off by filtration on a glass frit (removal of the remaining salts).

The filtrate is concentrated to dryness under vacuum to give 170 g of a crude product, which is purified by fractional distillation under vacuum. 157.4 g (yield: 92.5%) of the title product are obtained in the form of a yellow oil.

$n_D^{25°\ C.} = 1.5528$

B.p.$_{0.22\ mm\ Hg}$=72°–74° C.

(Comment: 0.22 mm Hg corresponds approximately to 29.3 Pa.)

Analyses by (i) thin layer chromatography (TLC) by means of silica gel and a mobile phase consisting of an 80/20 v/v cyclohexane/ethyl acetate mixture, and (ii) gas chromatography (CC), made it possible to demonstrate that the product of Example 1 (code no.: B-1 222) consists of a mixture of the E/Z geometrical isomers in the weight ratio and molar ratio of 91/9.

PREPARATION II

Preparation of
5-(1-methoxyiminoethyl)-4-methylthiazole
hydrochloride

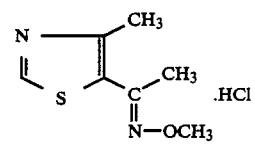

(Example 2; code no.: B-1 044)

17.02 g (0.1 mol) of B-1 222 obtained by method of preparation I above are dissolved in 200 ml of anhydrous diethyl ether. The resulting solution is cooled and saturated with a gaseous stream of dry HCl. The crystals formed are filtered off on a glass frit, washed with anhydrous diethyl ether and then dried under vacuum at 60° C. Recrystallization from ethyl acetate gives 18 g (yield: 87%) of the expected product in the form of white crystals.

M.p.$_{inst.}$=100°–105° C.

IR spectrum: conforms to the proposed structure
NMR spectrum: conforms to the proposed structure
TLC: 2 spots (E and Z isomers)
CC: 2 peaks (E and Z isomers)

Analyses by (i) thin layer chromatography (TLC) by means of silica gel and a mobile phase consisting of an 80/20 v/v cyclohexane/ethyl acetate mixture, and (ii) gas chromatography (GC), made it possible to demonstrate that the product of Example 2 (code no.: B-1 044) consists of a mixture of the E/Z geometrical isomers in the molar ratio of 90/10.

PREPARATION III

Preparation of
5-(1-n-butoxyiminoethyl)-4-methylthiazole

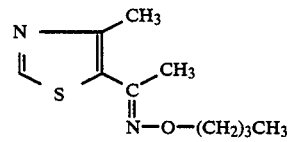

(Example 8; code no.: B-1 266)

15.61 g (0.1 mol) of 5-(1-hydroxyiminoethyl)-4-methylthiazole and 115 ml of butan-1-ol are introduced into a 500 ml three-necked flask provided with a condenser, a dropping funnel, a thermometer and a magnetic stirrer. 39.38 g (0.15 mol) of triphenylphosphine dissolved in 45 ml of tetrahydrofuran, and 34.86 g (0.2 mol) of diethyl azodicarboxylate dissolved in 65 ml of butan-1-ol, are added to the resulting mixture. The reaction medium obtained is stirred at room temperature (15°–20° C.) for 36 h. After the insoluble material has been separated off by filtration on a glass frit, the filtrate is evaporated to dryness under vacuum. The evaporation residue is taken up several times with hexane. The organic phases are combined and concentrated to dryness under vacuum. 20.2 g (yield: 95.1%) of the expected product are obtained in the form of a yellow oil. The IR spectrum conforms to the proposed structure. The product is a mixture of E and Z isomers in the weight ratio and molar ratio E/Z=89/11.

$n_D^{21°C.} = 1.5275$

PREPARATION IV

Preparation of 5-(1-n-butoxyiminoethyl)-4-methylthiazole hydrochloride (Example 9; code no.: B-1 233)

The free base obtained according to Preparation III is converted into an addition salt, namely the hydrochloride in the present case, by the method described in Preparation II. Recrystallization from a hexane/ethyl acetate mixture (1/1 v/v) gives the expected B-1 233 with a yield of about 85%.

M.p._inst._=68°–73° C.

The product is a mixture of E and Z isomers in the weight ratio and molar ratio E/Z=98/2.

PHARMACOLOGICAL TESTS

A number of tests undertaken with the compounds according to the invention by comparison with two reference anticonvulsants, namely sodium valproate (abbreviated to VALP) and trimethadione (abbreviated to TRIM), have been summarized below.

I-TOXICITY

The toxicity of the products to be studied was investigated by the oral administration, using an esophageal tube, of each of the said products to male mice with a body weight of 18 to 22 g, divided into groups each containing 10 to 20 animals. The mortality was recorded over a 14-day period.

The results obtained, which are expressed in the form of $LD_{50}$ in mg/kg, are collated in Table II below.

II-ANTICONVULSANT PROPERTIES

The anticonvulsant properties were investigated on male mice, thirty minutes after the oral administration of the substances to be studied, by the induction of convulsive seizures.

These seizures are caused either by the intraperitoneal injection of pentetrazole (125 mg/kg) or by electrical stimulation of the cornea (supra-maximal electroshock, abbreviated to MCE).

The results, expressed in the form of the 50% effective dose ($ED_{50}$) per os (dose protecting 50% of the animals), are collated in Table III below. They show that the products according to the invention exert a protective effect against convulsions which is at least as great as that of the two reference products (VALP and TRIM) when considering the $ED_{50}$ values.

TABLE II
ORAL TOXICITY IN MICE*

| Product | Code no. | $LD_{50}$ mg/kg |
|---|---|---|
| Ex. 1 | B-1 222 | 740 |
| Ex. 2 | B-1 044 | 1000 |
| Ex. 3 | B-1 234 | 570 |
| Ex. 4 | B-1 229 | 1000 |
| Ex. 5 | B-1 235 | 1000 |
| Ex. 6 | B-1 264 | >1000 |
| Ex. 7 | B-1 265 | >1000 |
| Ex. 8 | B-1 266 | 750 |
| Ex. 9 | B-1 233 | >1000 |
| Ex. 11 | B-1 255 | >1000 |
| Ex. 12 | B-1 262 | >1000 |
| Ex. 13 | B-1 375 | >1000 |
| Ex. 14 | B-1 376 | >1000 |
| Ex. 15 | B-1 379 | >1000 |
| Ex. 16 | B-1 377 | >1000 |
| Ex. 17 | B-1 378 | >1000 |
| Ex. 18 | B-1 290 | >1000 |
| Ex. 19 | B-1 329 | >1000 |
| Ex. 20 | B-1 296 | >1000 |
| Ex. 21 | B-1 304 | 360 |
| Ex. 22 | B-1 097 | >1000 |
| Ex. 23 | B-1 077 | >1000 |
| Ex. 24 | B-1 193 | >1000 |
| Ex. 25 | B-1 267 | >1000 |
| Ex. 26 | B-1 061 | >1000 |
| Ex. 27 | B-1 042 | 1000 |
| Ex. 28 | B- 876 | 1000 |
| Ex. 29 | B-1 026 | 1000 |
| VALP | — | 977 |
| TRTM | — | 2182 |

Note
* toxicity determined on groups each containing 10 to 20 male mice.

TABLE III
ANTICONVULSANT PROPERTIES IN MICE*

| Product | Code no. | $ED_{50}$ in respect of convulsions induced by PTZ mg/kg | MCE mg/kg |
|---|---|---|---|
| Ex. 1 | B-1 222 | 62 | 84 |
| Ex. 2 | B-1 044 | 72 | 100 |
| Ex. 3 | B-1 234 | 91 | 97 |
| Ex. 4 | B-1 229 | 120 | 150 |
| Ex. 5 | B-1 235 | 100 | 120 |
| Ex. 6 | B-1 264 | 112 | >200 |
| Ex. 7 | B-1 265 | 140 | >200 |
| Ex. 8 | B-1 266 | >200 | >200 |
| Ex. 9 | B-1 233 | 138 | 150 |
| Ex. 11 | B-1 255 | 46 | 78 |
| Ex. 12 | B-1 262 | 100 | 157 |
| Ex. 13 | B-1 375 | 105 | 184 |
| Ex. 14 | B-1 376 | 140 | >200 |
| Ex. 15 | B-1 379 | 60 | — |
| Ex. 16 | B-1 377 | 96 | >200 |
| Ex. 17 | B-1 378 | >200 | >200 |
| Ex. 18 | B-1 290 | >200 | >200 |
| Ex. 19 | B-1 329 | >200 | >200 |
| Ex. 20 | B-1 296 | >200 | >200 |
| Ex. 21 | B-1 304 | >200 | >200 |
| Ex. 22 | B-1 097 | >200 | >200 |
| Ex. 23 | B-1 077 | >200 | >200 |
| Ex. 24 | B-1 193 | >200 | >200 |
| Ex. 25 | B-1 267 | >200 | >200 |
| Ex. 26 | B-1 061 | >200 | >200 |
| Ex. 27 | B-1 042 | >200 | >200 |
| Ex. 28 | B- 876 | 126 | >200 |
| Ex. 29 | B-1 026 | 200 | >200 |
| VALP | — | 244 | 242 |
| TRIM | — | 251 | 500 |

Notes
PTZ: pentetrazole;
MCE: supra-maximal electroshock;
*: $ED_{50}$ in mg/kg, determined per os on groups each containing ten male mice.

III-NEUROTOXIC PROPERTIES

The neurotoxic properties were assessed on male mice by the so-called "Rota-rod" test carried out thirty minutes after the oral administration of the substances to be studied. The animals (divided into groups each containing ten male mice per dose and per product) are installed on the rod and their fall is observed over the next two minutes.

The results obtained are expressed in the form of the 50% neurotoxic dose ($TD_{50}$) per os, which is the dose causing 50% of the animals to fall. These results are collated in Table IV below, which, for comparison of the invention compounds with the above-mentioned reference products (VALP and TRIM), also gives the values of the ratios $TD_{50}/ED_{50}$ (protection index) and $LD_{50}/ED_{50}$ (therapeutic index), in which the $ED_{50}$ values are the 50% effective doses in respect of the convulsions induced by pentetrazole (PTZ) and supramaximal electroshock (CE), determined as indicated above (see Table III in particular).

The results in Table IV clearly show that, in particular, the protection indices and therapeutic indices of the compounds according to the invention of Ex. 1 (B-1 222), Ex. 5 (B-1 235), Ex. 11 (B-1 255), Ex. 12 (B-1 262), Ex. 13 (B-1 375) and Ex. 16 (B-1 377) are better than those of the reference products, namely sodium valproate and trimethadione, the most effective products according to the invention being the product of Example 11 (B-1 255) and the corresponding hydrochloride, and the product of Example 12 (B-1 262).

TABLE IV

| Product | Code no. | NEUROTOXIC ACTIVITY | | | | | |
|---|---|---|---|---|---|---|---|
| | | $TD_{50}$* mg/kg | Protection index | | $LD_{50}$ mg/kg | Therapeutic index | |
| | | | PTZ | MCE | | PTZ | MCE |
| Ex. 1 | B-1 222 | 347 | 5.6 | 4.1 | 740 | 11.9 | 8.8 |
| Ex. 2 | B-1 044 | 270 | 3.8 | 2.7 | 1000 | 13.9 | 10.0 |
| Ex. 3 | B-1 234 | 290 | 3.2 | 3.0 | 570 | 6.3 | 5.9 |
| Ex. 5 | B-1 235 | 750 | 7.5 | 6.3 | 1000 | 10.0 | 8.3 |
| Ex. 9 | B-1 233 | 600 | 4.4 | 4.0 | >1000 | >7.3 | >6.7 |
| Ex. 11 | B-1 255 | 1000 | 21.7 | 12.8 | >1000 | >21.7 | >12.8 |
| Ex. 12 | B-1 262 | 1353 | 13.5 | 8.6 | >1000 | >10.0 | >6.4 |
| Ex. 13 | B-1 375 | 750 | 7.1 | 4.0 | >1000 | >9.5 | >5.4 |
| Ex. 14 | B-1 376 | 750 | 5.4 | — | >1000 | >7.1 | — |
| Ex. 16 | B-1 377 | 1500 | 15.6 | — | >1000 | >10.4 | — |
| VALP | — | 670 | 2.7 | 2.8 | 977 | 4.0 | 4.0 |
| TRIM | — | 1000 | 4.0 | 2.0 | 2182 | 8.7 | 4.4 |

Notes
Protection index: $TD_{50}$ per os/$ED_{50}$ per os
Therapeutic index: $LD_{50}$ per os/$ED_{50}$ per os
*dose determined per os on groups each containing ten male mice.

What is claimed is:

1. An oxyiminothiazole compound selected from the group consisting of:
   (i) the 5-(1-alkoxyimino- and 1-hydroxyimino-ethyl)-4-methylthiazoles of the formula

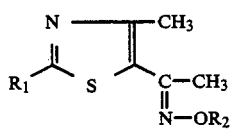

(1)

in which $R_1$ represents H, F, Cl, Br or $CH_3$ and $R_2$ represents a $C_1$-$C_{10}$-alkyl group, a benzyl group of the formula $CH_2C_6H_2(R_3)_3$, in which each $R_3$, identical or different, represents H, F, Cl, Br, $CF_3$, a $C_1$-$C_4$-alkyl group or a $C_1$-$C_4$-alkoxy group, a group $CH_2COOR_4$, in which $R_4$ represents H, a $C_1$-$C_4$-alkyl group or the ammonium group, $NH_4^+$, a group $CH_2COOM_m$, in which M is an alkali metal or alkaline earth metal and m is its valency, or a 2-aminoethyl group of the formula $CH_2CH_2NR_5R_6$, in which $R_5$ and $R_6$, which can be identical or different, each represent H or a $C_1$-$C_4$-alkyl group, it being possible for $R_5$ and $R_6$, taken together with the nitrogen atom to which they are bonded, to form a 5- to 7-membered N-heterocyclic group selected from the group consisting of pyrrolidino, piperidino, morpholino, thiomorpholino, 4-methylpiperazino, 4-phenylpiperazino, 4-(4-chlorophenyl)piperazino, 4-(2-hydroxyethyl)-piperazino and hexamethyleneimino groups, it also being possible for $R_2$ to represent the hydrogen atom when $R_1$ is other than H;
   (ii) the E and Z diastereoisomers thereof; and
   (iii) the corresponding addition salts.

2. An oxyiminothiazole compound according to claim 1 wherein $R_1$ is H, Cl, Br or $CH_3$.

3. An oxyiminothiazole compound according to claim 1 wherein $R_2$ is $CH_3$, $C_2H_5$, i—$C_3H_7$, n—$C_4H_9$, $CH_2C_6H_2(R_3)_3$ (in which each $R_3$, identical or different, is H, F, Cl, Br, $CF_3$, $CH_3$, $CH_3O$, or $C_2H_5O$), $CH_2COONa$, $CH_2COOK$, $CH_2COOCH_3$, $CH_2COOCH_2H_5$, $CH_2CH_2N(CH_3)_2$, $CH_2CH_2N(C_2H_5)_2$, 2-pyrrolidinoethyl, 2-morpholinoethyl or 2-piperidinoethyl, it being possible for $R_2$ to represent H if $R_1$ is other than H.

4. An oxyiminothiazole compound according to claim 1 wherein $R_2$ is $CH_3$, $C_2H_5$, i—$C_3H_7$, n—$C_4H_9$, $CH_2C_6H_4R_3$ (in which $R_3$ is H, F, Cl, Br, $CF_3$, $CH_3$, $CH_3O$ or $C_2H_5O$), $CH_2COONa$, $CH_2COOCH_3$, $CH_2COOC_2H_5$, $CH_2CH_2N(CH_3)_2$, $CH_2CH_2N(C_2H_5)_2$ or 2-pyrrolidinoethyl.

5. An oxyiminothiazole compound according to claim 1 which is selected from the group consisting of:
   (a) the E isomer and the Z isomer of 5-(1-methoxyiminoethyl)-4-methylthiazole and mixtures of the said E and Z isomers; and
   (b) the addition salts of the said E and Z isomers and of the said mixtures thereof, 6. An oxyiminothiazole compound according to claim 5 which consists of a mixture of the E and Z isomers of 5-(1-methoxyiminoethyl)-4-methylthiazole in the weight ratio E/Z=91/9.

7. An oxyiminothiazole compound according to claim 1 which is selected from the group consisting of:

(a) the E isomer and the Z isomer of 5-(1-benzyloxyiminoethyl)-4-methylthiazole and mixtures of the said E and Z isomers; and
(b) the addition salts of the said E and Z isomers and of the said mixtures thereof.

8. An oxyiminothiazole compound according to claim 7 which consists of a mixture of the E and Z isomers of 5-(1-benzyloxyiminoethyl)-4-methylthiazole in the weight ratio E/Z=89/11.

* * * * *